US008374832B1

(12) United States Patent
Kletecka et al.

(10) Patent No.: US 8,374,832 B1
(45) Date of Patent: Feb. 12, 2013

(54) VIRTUAL SCENE GENERATOR AND PROBABILITY OF INTERCEPTION SYSTEM AND METHOD

(75) Inventors: Christopher S. Kletecka, Willoughby Hills, OH (US); Patrick L. Ponsardin, Placitas, NM (US); Jeromy P. Rezac, Albuquerque, NM (US)

(73) Assignee: Exelis Inc., McLean, VA (US)

( * ) Notice: Subject to any disclaimer, the term of this patent is extended or adjusted under 35 U.S.C. 154(b) by 1467 days.

(21) Appl. No.: 11/951,679

(22) Filed: Dec. 6, 2007

Related U.S. Application Data (60) Provisional application No. 60/873,020, filed on Dec. 6, 2006.

(51) Int. Cl.
*G06G 7/48* (2006.01)
(52) U.S. Cl. .............................................. 703/6
(58) Field of Classification Search ........................ 703/6
See application file for complete search history.

(56) References Cited

U.S. PATENT DOCUMENTS

| 6,166,744 | A | 12/2000 | Jaszlics et al. |
| 7,048,384 | B2 | 5/2006 | Cole et al. |
| 7,430,046 | B2 * | 9/2008 | Jiang et al. ................ 356/336 |
| 2001/0027388 | A1 * | 10/2001 | Beverina et al. ................ 703/22 |
| 2003/0139662 | A1 * | 7/2003 | Seidman ........................ 600/407 |
| 2004/0015336 | A1 * | 1/2004 | Kulesz et al. ................... 703/11 |
| 2005/0009608 | A1 * | 1/2005 | Robarts et al. ................. 463/42 |
| 2006/0200330 | A1 * | 9/2006 | Suresh et al. ................... 703/11 |
| 2007/0273610 | A1 | 11/2007 | Baillot |
| 2008/0238916 | A1 * | 10/2008 | Ghosh et al. ................... 345/419 |

* cited by examiner

*Primary Examiner* — Dwin M Craig
(74) *Attorney, Agent, or Firm* — Edell, Shapiro & Finnan, LLC (57) ABSTRACT

Techniques are provided for simulating dissemination of at least one target substance in a scene that has been contaminated with the at least one target substance. Data is received from a user to select at least one target substance whose dissemination is to be simulated as well as parameters for the scene within which the simulation is to be performed. Simulation of the dissemination is performed and data can be displayed to illustrate, statistically and/or graphically, the results of the simulation. The simulation may include simulating interrogation of at least one surface in the scene with a sensor that detects ambient or scattered radiation from the at least one surface. Data may then be generated that indicates overlap of an interrogation spot of the sensor with the at least one target substance on at least one surface in the scene. A user may change parameters and repeat the simulation. The data generated by the simulation techniques is useful in designing sensors as well as developing strategies for deployment of sensors for certain applications.

25 Claims, 9 Drawing Sheets

VIRTUAL SCENE GENERATOR AND PROBABILITY OF INTERCEPTION SYSTEM AND METHOD

RELATED APPLICATIONS

This application claims priority to U.S. Application No. 60/873,020, filed Dec. 6, 2006, the entirety of which is incorporated herein by reference.

STATEMENT REGARDING FEDERALLY SPONSORED RESEARCH OR DEVELOPMENT

This invention was made with U.S. Government support under U.S. Government Contract No. 0886-J003ST050Y. The U.S. Government may have certain rights in the invention.

BACKGROUND OF THE INVENTION

There is a field of detection devices and systems designed to detect for the presence of substances harmful to humans, such as those used in chemical or biological warfare. During the design stage and prior to deployment, it is desirable to test and evaluate the performance of such detection systems. Since high-fidelity performance evaluation of active and passive remote sensors requires significant amounts of empirical data, one option is to test the detection systems in a real-world situation where a harmful substance is disseminated and the detection system is used to detect the substance.

Surface contamination can be the result of an accident or intentional dispersal of the contaminant, and therefore the surface contamination can consist of a single substance or multiple substances in bulk form or distributed over an area. Examples of persistent patches of contamination are bulk material, thin layers, small droplets or small particles.

Spectroscopy techniques are used to analyze substances and techniques have been developed for the non-destructive testing of surface-deposited substances in solid and liquid phases. Such techniques include Fourier Transform Infrared Spectroscopy (FTIR), X-ray fluorescence, gas chromatography and mass spectrometry (GC-MS), and Raman spectroscopy. Traditional surface hazard detectors include "point-and-shoot" devices, in which the device operator holds a sensing probe on a specific location. The performance of these kinds of detectors can be easily tested in the laboratory by exposing the sensor to variable doses of substances in a static mode. A new breed of surface contamination sensors based on the Laser Interrogation of Surface Agents (LISA) technique (as disclosed in U.S. Pat. No. 6,788,407 B1) affords new concepts of operation since these LISA sensors can probe the surface contaminants in near real time (~40 ms). This added capability translates into new ways of searching a potentially contaminated scene: systematic scan, random and adaptive scan strategies can be used to detect trace contaminants invisible to the naked eye. The performance of such devices will depend on a rich set of parameters such as, but not limited to, scan speed, scan patterns, contaminant distribution pattern and contamination type. Testing the effectiveness of such sensors in a realistic scene is costly, time-intensive and potentially dangerous.

Evaluation of a detection system can be more effectively performed using a computer model that accurately describes a user-selectable contamination scene and the interaction of a specific sensor configuration with that scene. Starting with a given contamination scene (i.e. substance types, size-distribution profiles, contamination densities, dispersal patches sizes and locations), performance metrics such as probability of detection and time-to-detect values can be quickly evaluated for a number of sensor configurations and operational scenarios. No other known model simultaneously tracks both substance dispersal positions and quantities along with substance properties and sensor interrogation and detection capabilities.

SUMMARY OF THE INVENTION

Briefly, the present invention is directed to simulating dissemination of at least one target substance in a scene that has been contaminated with the at least one target substance. Data is received from a user to select at least one target substance whose dissemination is to be simulated as well as parameters for the scene within which the simulation is to be performed. Simulation of the dissemination is performed and data can be displayed to illustrate, statistically and/or graphically, the results of the simulation. Furthermore, the simulation may further involve simulating interrogation of at least one surface in the scene with a sensor that detects ambient or scattered radiation from the at least one surface. Data may then be generated that indicates overlap of an interrogation spot of the sensor with the at least one target substance on at least one surface in the scene. A user may change parameters and repeat the simulation. The data generated by the simulation techniques is useful in designing sensors as well as developing strategies for deployment of sensors for certain applications.

DETAILED DESCRIPTION

Figure 1:
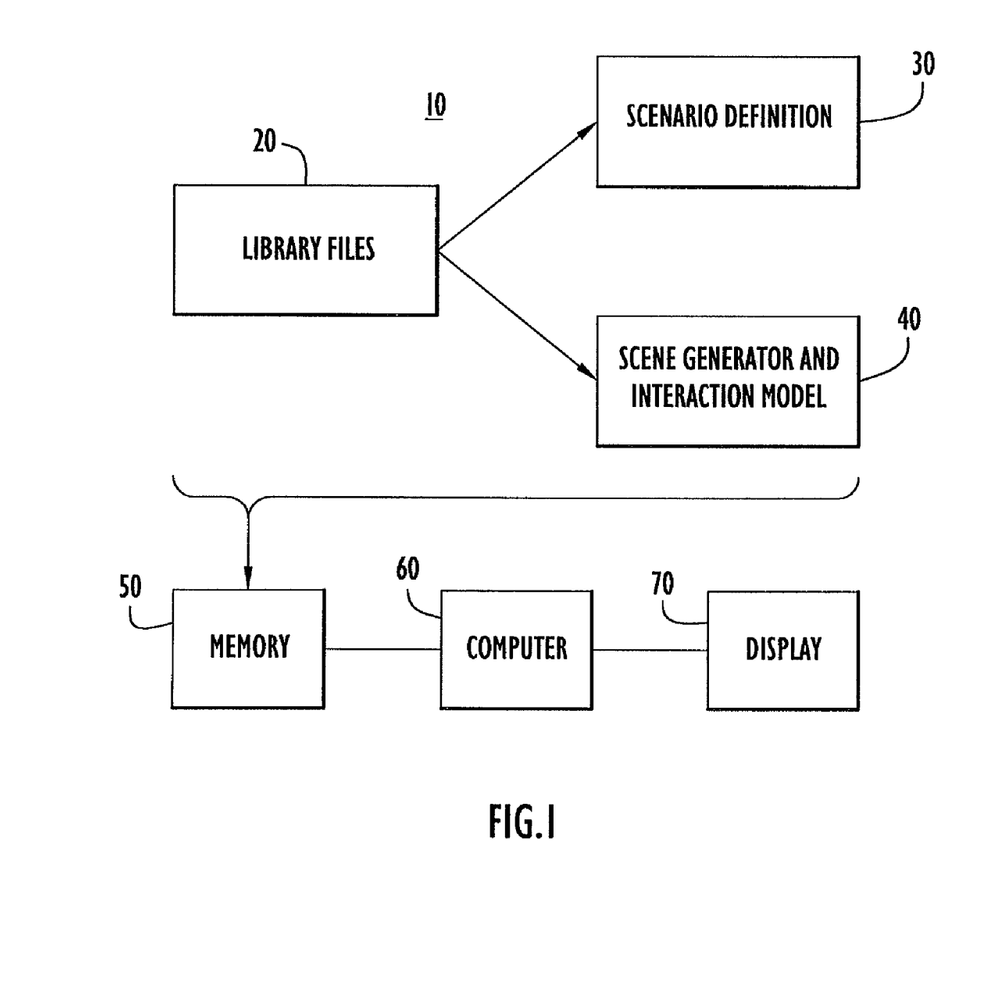
FIG. 1 is a block chart generally illustrating a virtual scene generator system and method according to an embodiment of the present invention.

Referring first to FIG. 1, a high-level block diagram of a virtual scene generation and probability of interaction analysis model system 10 according to an embodiment of the invention is shown. The system 10 is a computer-implemented system that comprises library files 20, scenario definitions 30 and a scene generation and interaction model 40. As shown in FIG. 1, the library files 20, scenario definitions 30 and scene generation and interaction model 40 are stored in one or more memories represented by memory 50. A computer 60, such as a personal computer or higher-power computer, connects to the memory 50 and executes computer software instructions to perform the functions of the scenario definitions 30 and model 40. The memory 50 may comprise (without limitation) a combination of one or more hard-drives, optical drives and one or more banks random access memory (RAM), for example. The computer 60 may comprise or more computing resources. A display monitor 70 is connected to the computer 60 to display results of the system 10.

The library files 20 consist of one or more databases of information related to various substances to be detected (hereinafter referred to as "target substances" or "target analytes"), interfering substances that can prevent detection of such target substances and particle size distributions of those substances. The library files 20 may be embodied as one or more databases managed by any database software. The scenario definitions 30 consists of data representing user-specified parameters for the type of sensor device/technology, which can be an active or passive device, to be tested and parameters for the scene in which the test is to be simulated. The scene parameters are described in further detail hereinafter. The scene generator and interaction model 40 is a computer software program that takes the scenario definition data and the relevant data from the library files 20 and executes a computer simulation of a contamination scene and operation of a sensor or detection system that either illuminates the contamination scene with a light beam and collects the return light, or passively accepts light from a localized space, according the user-specified sensor parameters to simulate remote detection of a target substance in the contamination scene. Thus, the scenario definition section 30 and the scene generator and interaction model 40 may be embodied by computer software stored in memory and executed by one or more computers.

The term "substance" or "analyte" as used herein may comprise any chemical or biological substance, or combination thereof and may be in liquid, solid, gas or aerosol form. Again, the terms "target substance" or "target analyte" refer the substance whose dissemination on the surface is to be modeled.

Figure 2:
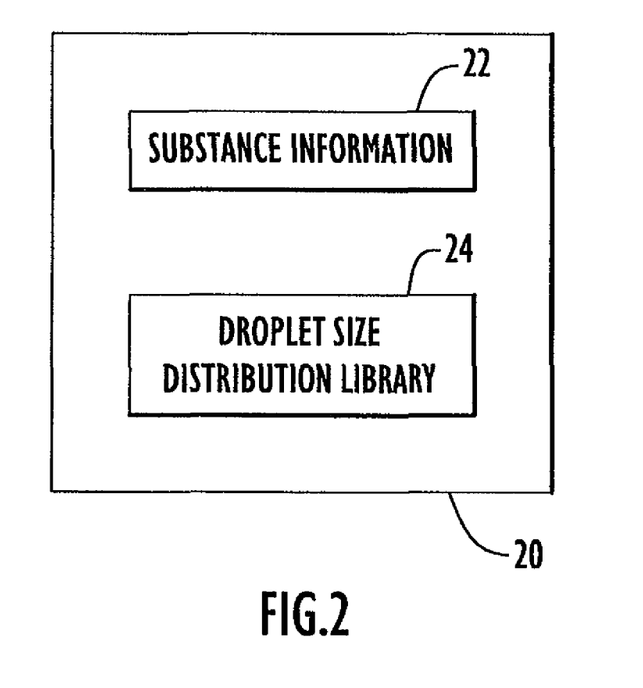
FIG. 2 is a block diagram illustrating library files according to an embodiment of the invention.
Figure 3:
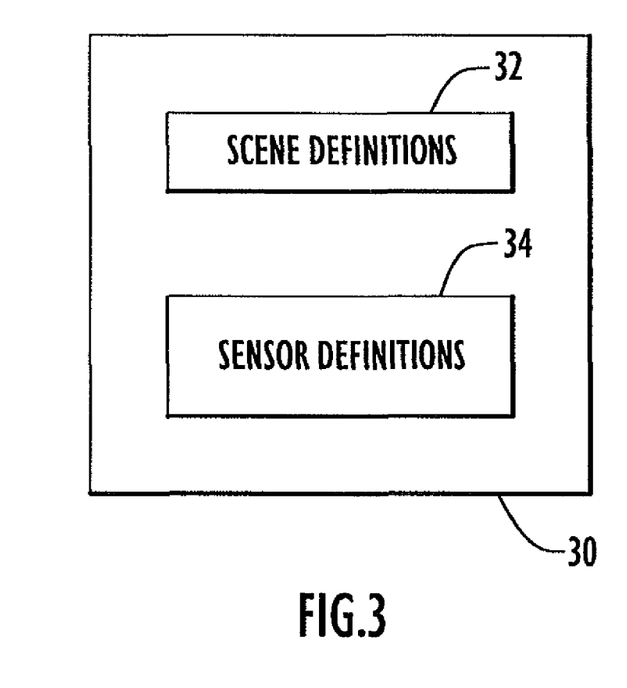
FIG. 3 is a block diagram illustrating scenario definitions according to an embodiment of the invention.

Turning to FIGS. 2 and 3, the library files 20 and scenario definition section 30 are described in greater detail. The library files 20 comprise target substance information 22 and a droplet size distribution library 24. The target substance information 22 comprises information identifying or characterizing numerous chemical or biological substances, such as those that are known to be harmful to humans. The substance information 22 may include, for example, density, molecular weight, air-to-surface adsorption spread factors, $ED_{50}$ limits (dose of a substance that is pharmacologically effective for 50% of the population exposed to the substance or a 50% response in a biological system that is exposed to the substance), $LD_{50}$ limits (lethal dose of a substance required to kill half the members of a tested population), vapor pressure, etc. It should be understood that to the extent the simulation is to account for interferents mixed with the target analyte that may mask the target analyte, the substance information 22 would also include data pertaining to such interferents.

The droplet size distribution library 24 contains statistical data regarding dissemination of the various substances in the substance information 22. Data in the library 24 may be compiled from research, from dissemination models, or from transport and dispersion models. The droplet size distribution data is used to provide a user defined number of droplet sizes within an overall distribution. Depending on the scenario, the droplet size distribution data may be a function of position in the scene.

The scenario definitions 30 comprise user specified scene definitions 32 and user specified sensor definitions 34. The scene definitions 32 are user-specified parameters or variables that describe the contamination scene and comprise, by way of example only, one or more of the following.

Single Substance Selection and Quantity. A single user-specified target substance and amount (in mass or volume) to be used in the simulation.

Multiple Substance Selections and Quantities. Several user-specified target substances and their respective amounts to be used in the simulation.

Interferent Selection and Quantity. The user-specified interfering substance(s) and amount(s) to be used in the simulation. An interfering substance is a substance that has known properties (e.g., Raman or fluorescence signature) and that interferes with ability of the sensor or detector to detect the target substance(s). Interferents can occur intentionally (e.g., by mixing highly fluorescent, non-reactive substances with a dangerous one to mask the signature or properties of the dangerous one), or unintentionally (e.g., diesel soot has a strong Raman signature in the band commonly used to identify various chemical substances).

Background Material. The user-specified background material is the material that comprises the surface being interrogated. For example, if the simulation to be run involves a detector that scans a wall for contaminants, the background material is paint, drywall or plaster, or a combination thereof. The background material has a signature that needs to be mixed with the signature of any surface contaminant substance. Other examples of background material include asphalt, concrete, carpet, etc. In addition, the background, in the case of chemical contamination, can potentially increase or decrease the rate of evaporation of the contamination.

Analyte Size Distribution. The user-specified droplet size distribution. This quantity may have a position dependence due to physical mechanics (e.g., due to gravity a vertical wall may have a larger relative quantity of large droplets lower on the wall) or certain dissemination techniques.

Surface Density. The user-specified contaminant surface density. The surface density may have a position dependence due to physical mechanics or certain dissemination techniques (e.g., dissemination from an explosion may have large quantity of contaminant close to the blast and comparatively little contaminant further away from the explosion.

Scene Size and Resolution. The user-specified area of the contaminated scene (contamination area) size and the smallest possible measurement to control the fidelity of the measurements and the time allotted to run the simulation. Alternatively, the model can simulate the physics with closed form integration—eliminating the need for digitization and scene resolution.

Contaminated Region. The user-specified localized area of contamination associated with the target substance(s) within the larger scene is described by the Scene Size variable explained above.

The sensor definitions 34 comprises user-specified parameters associated with the sensor that is to be used in the simulation for interrogating (overlapping) with the target analyte(s) on the surface. The sensor that is used in the simulation may be an active interrogation sensor or a passive interrogation sensor. An active interrogation sensor emits an interrogating signal, such as a light beam, towards a surface and detects radiation that is scattered by the light beam. By contrast, a passive interrogation sensor detects radiation that may be emitted from a surface as a result of the type of analyte on the surface. Since this model simulates overlap, it does not matter if the overlap comes from a laser and droplet or a droplet with a passive telescope.

Since the interaction model 40 simulates overlap with a substance, it does not matter if the overlap is between the field of view of an active sensor and substance or between the field of view of a passive sensor and the substance. For example, a passive sensor may comprise a telescope which has a field of regard that is on the order of millimeters or centimeters. Such a sensor could be used in the ultraviolet (UV) region to detect a very "hot" material that was emitting in the UV region. Similarly, a passive sensor with a similar telescope could be used in the mid or long wavelength infrared (IR) region to detect photon-producing molecular transitions or either blackbody radiation or absorptions within the blackbody spectrum.

In the case of an active sensor for example, the sensor definitions 34 may comprise data specifying the diameter of a light beam spot on the surface, the spatially dependent weighting factor of the light beam (could be a laser $M^2$ factor, a telescope field of regard factor, etc.), pulse repetition frequency (PRF) of a light source, surface scan speed, depth of field of the telescope that is used to capture the scattered radiation, and integration time. The PRF indicates the number of pulses of the light beam that may be illuminated on the surface during a certain time interval, e.g., per unit time. The scan speed is the speed at which the light beam spot may be moved across the surface, e.g., distance per unit time. One example of an active interrogation sensor is a laser interrogation sensor described in the aforementioned commonly assigned U.S. Pat. No. 6,788,407 B1.

For an active interrogation sensor, the model 40 may be designed to simulate the probability of interaction (i.e., overlap) of a light beam spot on the surface, wherein the light beam is produced by any type of technology. For example, Raman and fluorescence detection techniques involve interrogating a surface with a beam of light from, e.g., a laser, in various wavelength regions. In one example, the beam of light may be in the ultraviolet wavelength region. The light beam interacts with the substance(s) on the surface and scatters back or returns optical energy in certain wavelength regions depending on the chemical or biological make-up of the substance(s). The returned optical energy is also referred to as the signature. In a spectroscopy-based detection system, the constituent wavelengths of the returned optical energy are separated out by a spectrograph and measured. A prerequisite for these detection technologies to function at all is that the light beam actually intercepts a target analyte.

In the case of a passive interrogation sensor in which no interrogation light is emitted onto the surface that is being scanned, the sensor collects ambient light emanating from a localized, potentially contaminated surface by means of an optical collection device, such as a telescope. For example, the passive sensor may collect infrared (IR) light, such as light in the mid or far IR region, or thermal light that is emitted due to the blackbody characteristics of the surface or the material in order to identify a contaminant based on the contaminant's vibrational absorption, rotational absorption, or a combination of rotational and vibrational absorption spectra. It should be understood that the system and method according to the present invention is not limited to any particular type of detection or sensor technology, whether the sensor operates by active or passive interrogation.

Sensor definitions 34 for a passive interrogation sensor may include diameter of the field of view or regard of the sensor, surface scan speed, depth of field of the telescope or other receiving device, and integration time.

Figure 4:
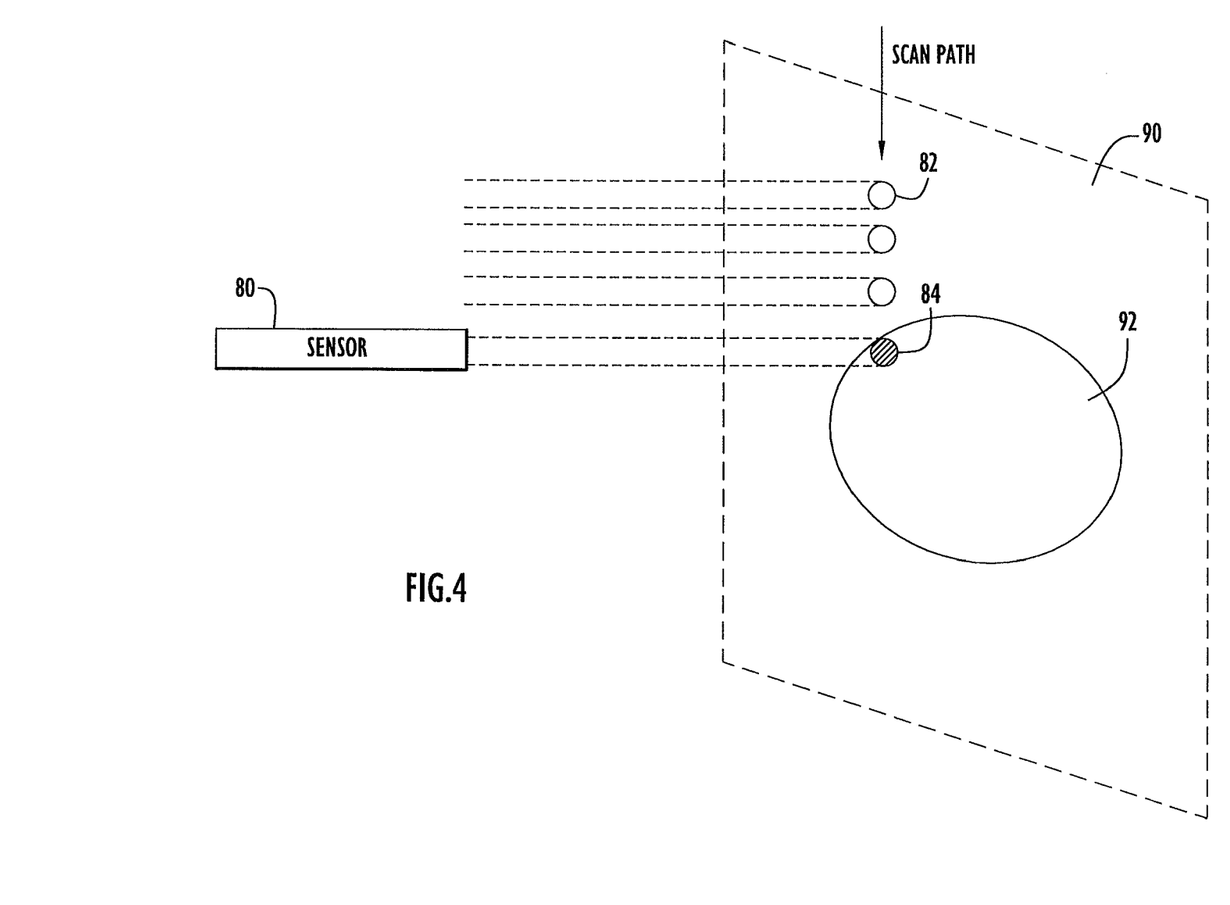
FIG. 4 is a diagram that generally depicts the scene that is simulated by the virtual scene generator system and method according to embodiments of the present invention.

Turning now to FIG. 4, a diagram is shown that depicts the environment that the virtual scene generation techniques are used to simulate in accordance with one example. There is a sensor 80 whose performance is to be evaluated for detecting one or more analytes dispersed on a surface shown at 90. For illustration purposes, the dispersion of the one or more analytes is shown at 92. The sensor 90 may be an active or passive sensor and is scanned across the surface 90 in order to detect for the presence of an analyte. FIG. 4 shows one scan path where a field of regard or "view" of the sensor 80 is shown at 82. For clarity, any potential smearing of the detection spot due to the integration time is not shown. An illustrative overlap between the field of regard of the sensor 80 and one or more of the target analytes is shown at 84.

Figure 5:
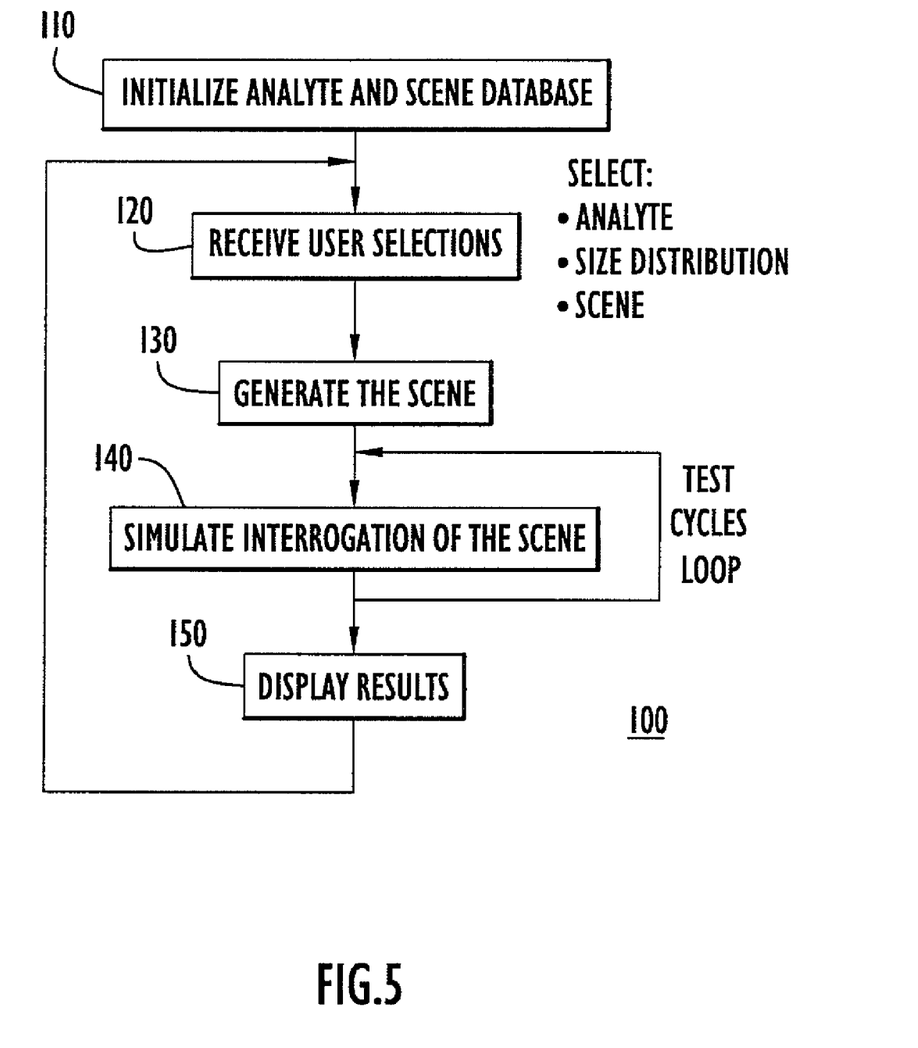
FIG. 5 is a high level flow chart that depicts operation of the virtual scene generator according to an embodiment

Referring now to FIG. 5, a process 100 is described for performing the virtual scene generation techniques. The process 100 comprises at 110 initializing the analyte and scene databases—those library files shown in FIGS. 2 and 3. Next, at 120 the process waits to receive selections from a user for one or more analyte(s), intereferents, etc., to be used in a simulation, size distribution data for the simulation and scene definitions for the simulation. As described above, when selecting an analyte a user may select one or more analytes, one or more interferents, and background materials. When selecting a size distribution, the user may select the size distribution of dispersed analyte(s) and the quantity of dispersed analyte(s). When selecting scene parameters, the user may select the scene resolution (also referred to as the matrix resolution) or closed form integration option, the scene size, the center position of the contamination region (random or user-selected), interrogation patch diameter, PRF, scan speed and integration time. At 130, the scene to be simulated is generated based on the user selections. At 140, interrogation of the scene is simulated and at 150 results of the interrogated scene are displayed to a user. The scene generator and interaction model 40 (FIG. 1) performs the functions shown at 130 and 140. Examples of output data are the interrogation number (mission time, i.e., running count of the number interrogation simulated), coordinates, chemicals present, and percentage overlap with the chemicals, total pixel value of the overlap. All of this data is written to a file. Again, as described above, the interrogation that is simulated may be an active interrogation (e.g., using a laser or other interrogated light) or a passive interrogation where ambient light is collected from the simulated contaminated scene.

One embodiment of the scene generation and probability of interaction model 40 is described in further detail with reference to FIG. 6. In other words, FIG. 6 illustrates in more detail the functions performed by the scene generation function 130 and the interrogation simulation function 140 shown in FIG. 4.

Generally, the model 40 uses data about various chemical and/or biological substances from the library files 20 and randomly distributes the target substance(s) (analytes) as it/they would be disseminated in the real-world on the surface called a virtual surface. The model 40 then runs simulated interrogations of the surface with the user-specified sensor system characteristics to test operation of the sensor system's interception of the target substance(s). The model is not limited to a two dimensional (2-D) virtual surface, as it can map, track the properties, and interrogate contaminants in a three dimensional (3-D) virtual environment. Four dimensional (4-D) tracking is also possible, since the characteristics of the contaminants may change with time (e.g., evaporate). For example, one or more of the analytes and interferents and background material involved in a simulation can evolve over time due to forces, physical properties, or physical phenomena including, but not limited to, gravity, evaporation, re-condensation, etc. In any of the embodiments described herein, the interrogation disc-substance droplet (or particle) integration is a volume integration that would take into consideration the volume of the substance and the spatial properties of the interrogation spot.

Figure 6:
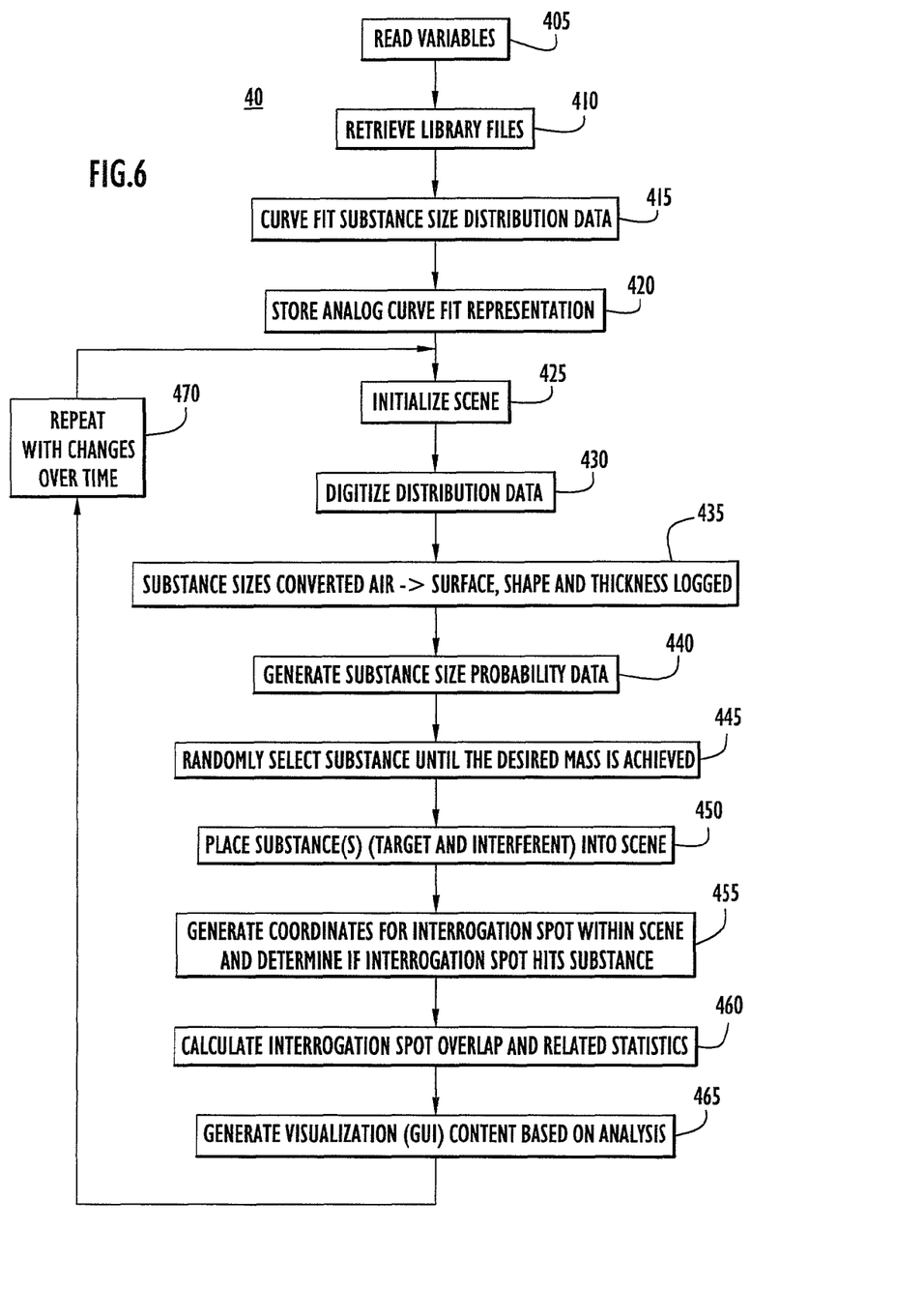
FIG. 6 is a flow chart illustrating the scene generator and probability of interaction model according to an embodiment of the invention.

As shown in FIG. 6, after the scenario definition phase is complete, execution of the model 40 begins at 405 with reading the variables established by the user in the scenario definition (at 120 in FIG. 4). Next, based on the variables in the scenario definition, at 410 the data related to the target substance(s), interfering substance(s) (if any) and other parameters from the scenario definitions are retrieved from the library files. The term "particle" is used herein to represent a small amount of target substance or interfering substance, in liquid or solid form, after dissemination. At 415, the model 40 curve fits particle size distribution data to the user-specified particle size distribution of the target substance(s) and interfering substance(s), if any. The target (and interfering) substance(s), when disseminated, can have an infinite variety of particle size distributions. Variables affecting the size distribution include (but are not limited to): dissemination mechanism (spray, explosion, evaporation and re-condensation, etc.), wind conditions (currents), temperature, and chemical properties. At 420, after curve fitting the particle size distribution, the curve fit is stored as an analog function for later digitization. In one embodiment of the model 40, steps 415 and 420 may not be necessary if the user selects or provides a size distribution that is represented by a mathematical function as opposed to a data file (e.g., two column probability vector).

A matrix, as it is used herein, is a mechanism used to group a set of numbers or data that describe a physical or mathematical entity. These are not matrices in the linear algebra sense, but serve as data organizers and descriptors. For example, the droplet size distribution matrix is a set of data that describes the sizes of droplets (aerosolized or not) that are most likely to encountered—in a particular scenario. The matrix is two columns of data, droplet sizes and their corresponding normalized probability of occurrence.

The scene matrix is a set of data representing two or three dimensional coordinates that locates every fundamental unit of the scene. The user can select the resolution of the scene matrix with the Scene Resolution parameter. This is useful because large analyte areas and larger interrogation beam diameters would not need high resolution, whereas small analyte areas and interrogation light beam diameters would need higher resolution. As mentioned in the foregoing, there may be applications that require higher fidelity and thus require that the interrogation beam-surface contaminant integration be calculated in closed form, making the digitization of the scene unnecessary. In this case, as can be the case in the digitized form, the integration can be a volume integration, taking into consideration the spatial properties of the particle, the spatial intensity factors of the light beam (if an active interrogation sensor is used), and the relative positions of the light beam and the analyte. In most cases, the closed-form integration will require more model processing yielding a fidelity vs. processing time balance/evaluation.

At 425, the model accesses the user specified inputs regarding the scene and calculates how many data points are required in the scene based on the Scene Size and Scene Resolution to produce the scene matrix. As explained above, each data point in the scene can be represented by two coordinates, or three coordinates in the case of a 3-D scene simulation. However, only surface contaminants (target substances and interfering substances) are given coordinates at subsequent stages of the model processing. Any coordinate not in the contaminant registry is assumed to be background only. Also, at this point, the program determines if the interrogation sensor has a shot-to-shot spatial overlap of two consecutive interrogation spots based on scan speed and pulse repetition frequency (to reduce the data storage needed for the computation results). The background material parameters for the virtual surface are read from the user definitions and the material properties from the library files are loaded into the registry.

At 430, the program digitizes the size distribution analog function for the one or more target substances and zero or more interfering substances based upon the number of sizes the user specifies for each target substance and interfering substance involved in the simulation. The particles of the target substance(s) and interfering substance(s) (if any) are assigned properties (particle property data) that they will likely have once adsorbed onto the virtual surface of a 2-D scene or virtual surfaces of a 3-D scene. At 435, information about surface, shape, and thickness (size) of the particles is logged by assigning coordinates to each contaminated data point. A separate matrix (data set) is created to track the particle property data, i.e., shape and thickness of the target analyte at each coordinate data point.

At 440, an algorithm is executed that takes the digitized distribution data for the target substance(s) (and interferent substance(s), if one or more interfering substance are involved in the simulation) and creates a probability matrix (data set), where each size of a target substance (and interfering substance) particle is allocated a number of slots in the probability data set proportional to the probability of it occurring. A purely random process selecting sizes from the matrix an infinite number of times would return the original target substance (and interferent substance) distribution matrix.

At 445, an algorithm is executed that randomly or pseudo-randomly selects sizes of one or more target substance(s) (and interfering substance(s)) from the probability matrices developed at 440. The size and mass of the s particles are recorded into a registry data file to await placement into the scene matrix (which occurs in 450). This process of selecting sizes concludes when the integrated (total) mass of all of the selected particles equals the user specified total mass. This step is performed for each substance and interferent in each contaminated region. For example, at 445, particles of each target substance are randomly or pseudo-randomly placed at positions with respect to a center or other user-specified dissemination point (coordinate) in the scene. In one implementation, the scene is divided into concentric rings (or spheres) moving outward from the dissemination point and particles are randomly placed at positions within concentric rings (or spheres) such that rings or spheres closer to the dissemination point will have a greater concentration of particles, and the concentration of particles progressively decreases in rings or spheres that are further from the dissemination point. The same is performed for each interfering substance.

In certain circumstances it is useful to choose coordinates for the interrogation source (455) prior to choosing coordinates for the substance droplets (450). The model 400 determines which method is more time advantageous and executes appropriately.

At 450, the data representing particles for the one or more target substances and particles for the zero or more interfering substance are placed into the scene based upon the user selections in 120 for each of target substance (and interferents) particles stored from the random particle selection at 445.

Next, at 455, the program generates start coordinates for the interrogation spot within the scene and determines if the interrogation spot hits a particle for a target substance and interfering substance. A scan pattern may be automatically selected or a user-specified scan pattern may be executed. After each placement of the interrogation spot on the surface based on the scan speed, it is determined if the interrogation spot overlaps with (the spot hits) the target substance. The model may also determine whether the interrogation spot overlaps with an interfering substance. If no overlap (hit) occurs, the algorithm reports the data as a "miss". If an overlap occurs, the algorithm breaks its loop and initializes the next process 460 to determine overlap statistics, but the procedure at 455 is re-engaged after the process 460 has computed the overlap statistics.

More specifically, in one implementation, each surface in the scene is assigned an identifier (e.g., a number). Thus, if the scene is two-dimensional, then there is only one surface, whereas if the scene is three-dimensional there are multiple surfaces. Each point in one a surface is defined by a pair of coordinates (X-Coordinate, Y-Coordinate) and a radius.

The X-coordinates are sorted (with each other member of the row maintaining the connection to the respective X-coordinate) so that the analyte particles are aligned in a sequential fashion for each surface. The purpose for sorting the data in this way is to expedite the process of determining overlap of particle and interrogation spot. The analyte arrays are now prepared for the interrogation spot to begin probing the surface.

The interrogation spot is given a new set of center coordinates (based on the parameters of the user-specified scan pattern) and the comparison begins. For the relevant surface, the X-coordinate of the diameter of the interrogation spot is projected onto the scene matrix that has been populated with data representing particles for the target substance(s) and interfering substances, if any.

The process records into a separate data set any target substances and interfering substances that have an X-coordinate (+ or − the radius of the target substance particle) which overlaps the X-coordinate of the interrogation spot (+ or − the radius of the interrogation spot). If there are no overlaps, the interrogation spot is given a new set of center coordinates and the comparison repeated.

If there is an overlap or overlaps, the target substances and interfering substances that are overlapped are saved into a new X-coordinate comparison data set, then the saved target substances and interfering substances are compared to the Y-axis. If any droplets have Y-coordinates (+ or − the radius of the droplet) which overlap the Y-coordinate (+ or − the radius of the interrogation spot) of the interrogation spot, then those analytes (target and/or interfering) are recorded in a final comparison data set. If there are no overlaps, the process proceeds to assigning a new center position to the interrogation spot as described above and the X and Y comparison data sets are purged.

If there is an overlap or overlaps, the process continues as described below. Up until now, the way the projection occurred (the projection of the circle was a square, yielding too much area), there may still be no overlap and this is investigated as follows.

For a closed form integration computation, this part of the process begins with the X and Y coordinate comparison data set and coordinates for the interrogation spot. Closed form integration can be performed in two-dimension or three-dimensions depending on the desired result (volume or surface). The two-dimensional integral is a surface integral that calculates the common area overlap. The three-dimensional integral takes into consideration the surface of the analyte and the spatial weighting function of the interrogation spot, performs the volume integral and returns the volume overlap.

For a digital overlap computation, this part also begins with the X and Y coordinate comparison data set and coordinates for the interrogation spot. Digitally the same process occurs as in closed form integration, except the program counts the number of pixels (voxels in the 3-D case) that overlap, either in two-dimensions or three-dimensions, this time by geometry and not calculus. Each pixel is considered, sequentially, and when a pixel is determined to be within the boundaries of each surface (2-D or 3-D), then it is recorded as a hit or overlap. Each common pixel is recorded.

At 460, the nature of the overlap of the interrogation spot and a particle is computed to produce statistics regarding the "hit". Examples of statistics that may be produced at 460 are:

1. Number of hits (interceptions) of the interrogation spot with an (analyte or interferent) in a contaminated region of a scene over total number of interrogations. Statistics drawn from this data: Percentage of pure target analyte interception (over total number of interrogations) or Percentage of pure interferent interception (over total number of interrogations).

2. Simultaneous interceptions of an analyte and an interferent in a contaminated region of a scene over total number interrogations. Statistics drawn from this data: Mix interception (hit) percentage.

3: In the case of an active sensor, overlap of the light beam (with analyte or interferent) per interrogation pulse of the light beam. Statistics drawn from this data: Pure (analyte/interferent) average overlap area.

4. Overlap of interrogation spot with analyte and interferent per interrogation. Statistic drawn from this data: Mix analyte-interferent average overlap area 5. Particle sizes of "hits". Statistics drawn from this data: Particle sizes most likely to be interrogated by sensor.

6. All interrogations (hits and misses) while source is scanning over a contaminated region. Statistics drawn from this data: Time needed to scan over a contaminated region and record a hit with a certain probability of a hit occurring.

7. Hits of analyte to hits of interferent (or hits of analyte and interferent) Statistics drawn from this data: Amount of interferent needed to severely limit the usefulness of the sensor.

At 465, display content data is generated based on the analysis of the processes. Generation of GUI content may occur in real-time during the various processes shown in FIG. 4, or display content can be disabled so that a simulation can be run faster and produce a minimal amount of display content only at the completion of the simulation.

As explained above and shown at 470, relevant ones of the computations shown in the flow chart of FIG. 6 may be repeated to simulate changes to the target substance(s) and interferents(s) over time as a result of forces, physical properties or physical phenomena including, but not limited to, gravity, evaporation and re-condensation.

Figure 7:
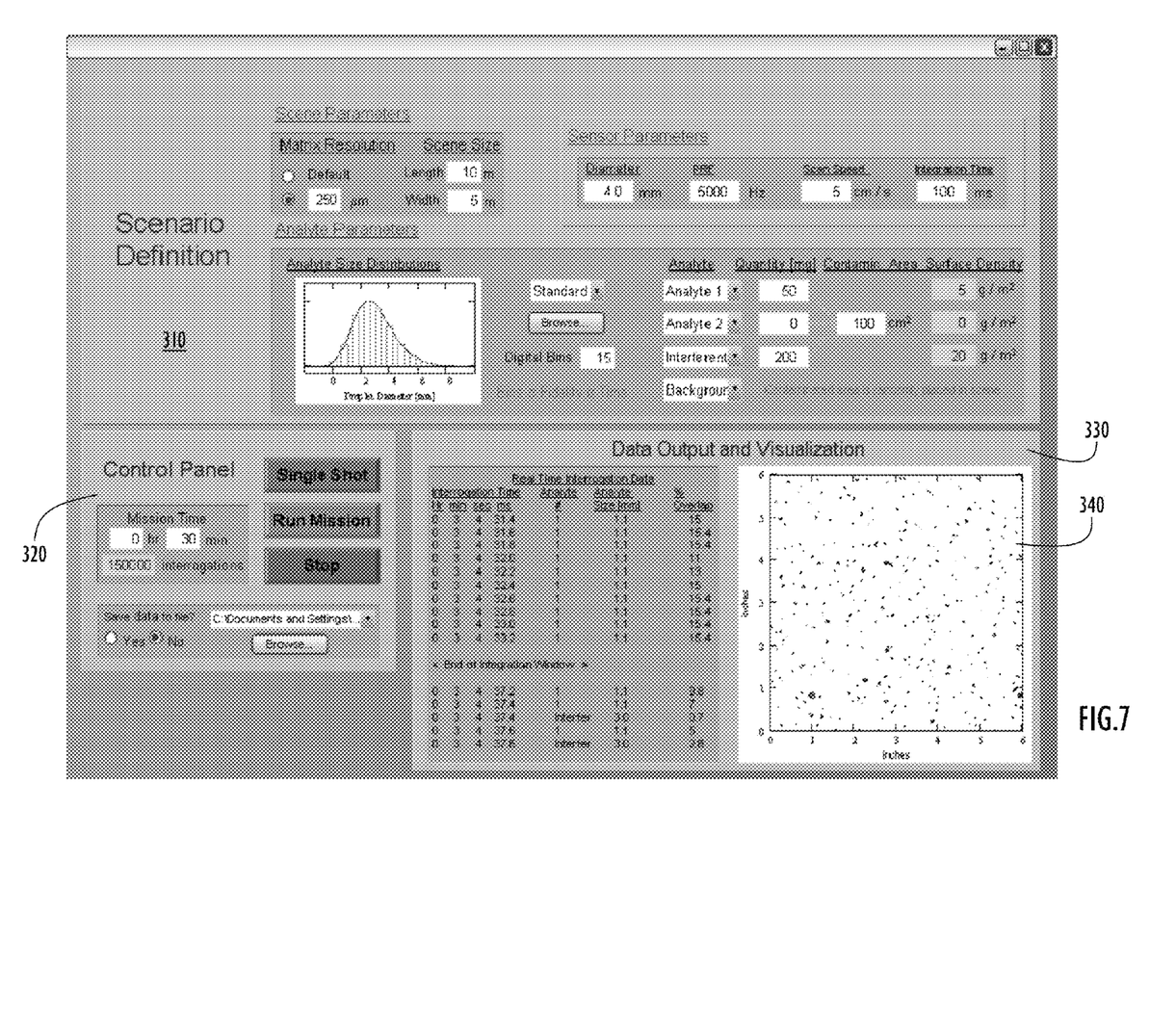
FIG. 7 is a screen shot showing an example of a graphical user interface for user selection of scenario definition parameters and display of output data according to an embodiment of the invention.

FIG. 7 is a screen shot showing an example of a graphical user interface (GUI) display screen for receiving scenario definition data from a user and for displaying results of a simulation. There is a Scene Definition window 310 that allows a user to select parameters for the scene, analyte(s) and sensor. The display screen also comprises a control panel window 320 comprising buttons to run a "single shot" interrogation where a single interrogation or a mission according to user configurable parameters for the time and number of interrogations of a mission. There is also a "run" button to initiate a single shot or mission and to stop either. The display screen also comprises a data output and visualization window 330 that displays real-time interrogation data in tabular form and also an interrogation map 340 that shows the areas of the scene where interrogations are made.

Figure 8:
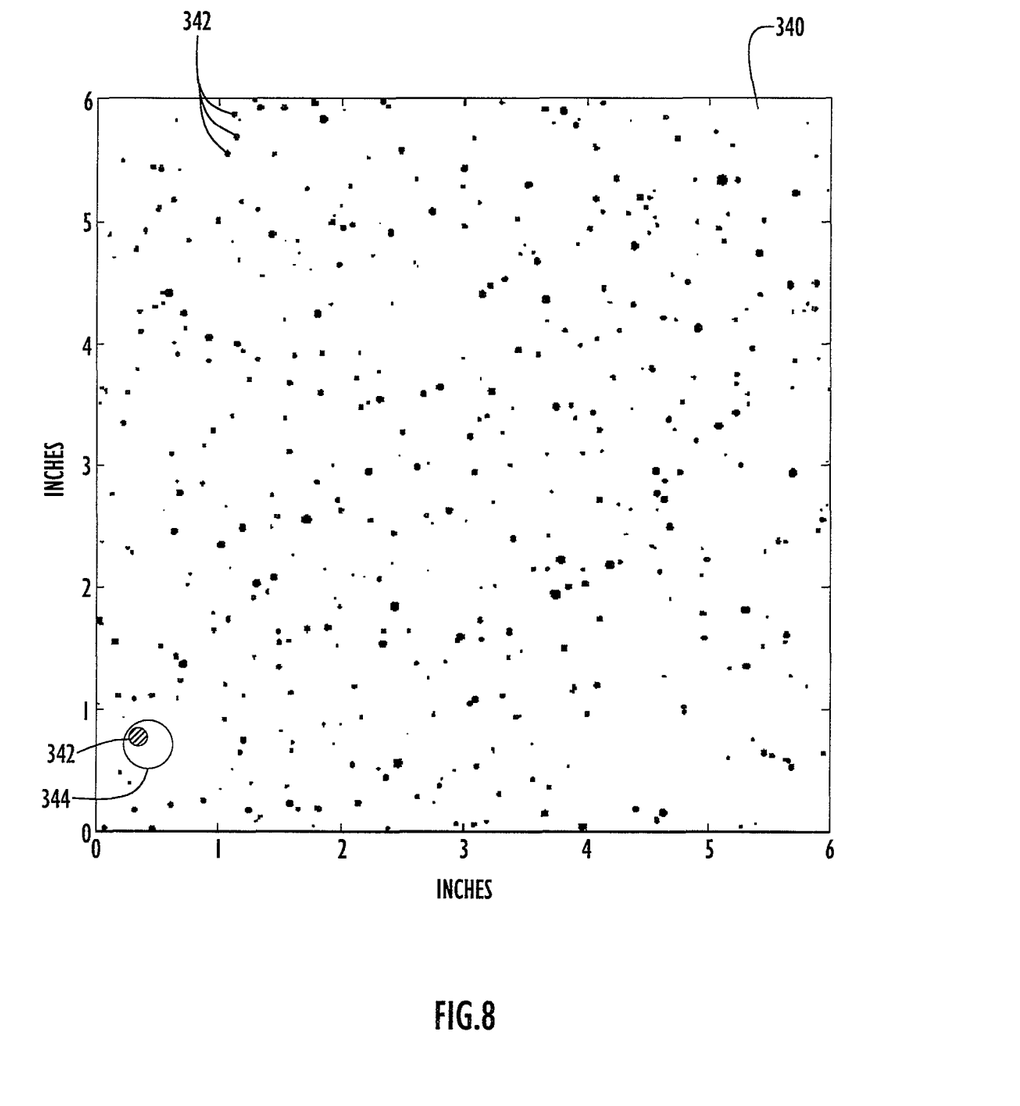
FIG. 8 is a diagram showing an example of interrogation map showing positions of droplets and an interrogation spot of a sensor.

FIG. 8 illustrates an example of an interrogation map 340 in enlarged form. The dots shown at reference numeral 342 represent positions of particles of one or more target substances (and interfering substances if any are involved in the simulation). An interrogation spot of a sensor is shown at reference numeral 344. Thus, FIG. 8 shows that there is an overlap between an interrogation spot and a target substance particle.

Figure 9:
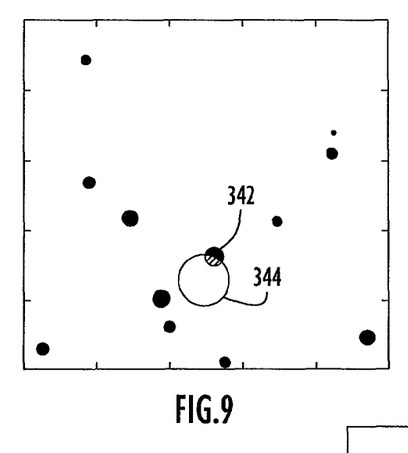
FIGS. 9-11 are diagrams showing examples of overlap between an interrogation spot and droplets.
Figure 10:
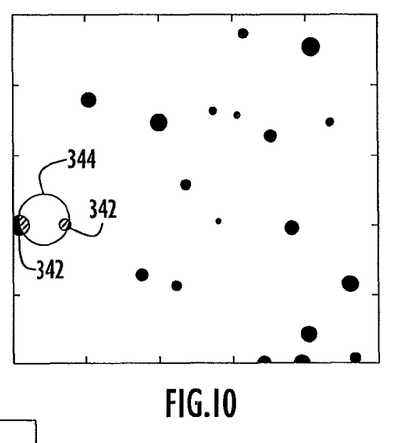
Figure 11:
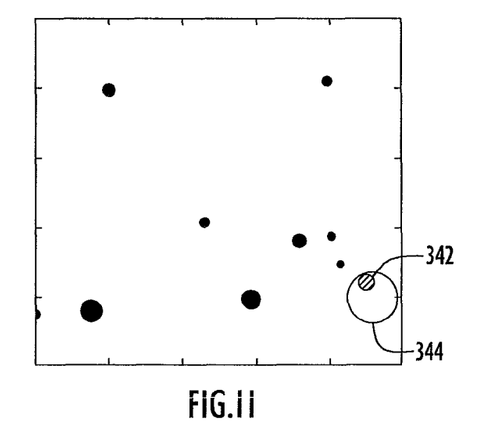

FIGS. 9-11 illustrate further examples of possible occurrences that are displayed in an interrogation map. FIG. 9 shows partial overlap between the interrogation spot 344 and a target analyte particle 342. FIG. 10 shows partial overlap between the interrogation spot 344 and two target analyte particles 342. FIG. 11 shows complete overlap between the interrogation spot 344 and a target analyte particle 342. Color coding may be used to distinguish dots that represent particles 342 from the larger dot that represents the interrogation spot 344. In addition, color may also be used to show the overlap between the interrogation spot 344 and a particle 342. For simplicity, a cross hatching is used to show the overlap in FIGS. 9-11.

The data and statistics listed above are only examples of the types of useful output of the system and method according to the present invention. Moreover, the present invention has the dual advantage of providing useful data for front end detection/sensor system design (using more generalized statistics) and post design analysis (using derived return signal strengths for use in a sensor performance model). Further still, the system and method are useful in training individuals on the use of detection equipment, assisting in designing scanning strategies for certain real-world scenarios and training a software algorithm in a detection system without having to take the system into the field which is costly and dangerous.

The techniques described herein can also be used to simulate interrogations from multiple sensors (passive and/or active) used simultaneously, i.e., multiple sensors operating in tandem. In this application, the output statistics and interrogation map may be provided separately for each sensor and combined for all sensors.

The system may be run several times in order to generate a statistically relevant description of the contaminated scene. The user can easily change the scene parameters and re-run the simulation. By contrast, to generate contaminated scenes experimentally would require expensive and time consuming steps of: (1) spraying a witness card; (2) evaluate the witness card to be sure sufficient analyte surface concentration; (3) interrogate witness card with proper interrogation beam diameter; (4) photographically record the interrogation event; (5) load photographic record into a computer to analyze the interrogation event and estimate overlap (in the event overlap actually occurred); (6) log the data; and (7) repeat steps 1-6 to generate sufficient data to build statistics of the events.

Figure 12:
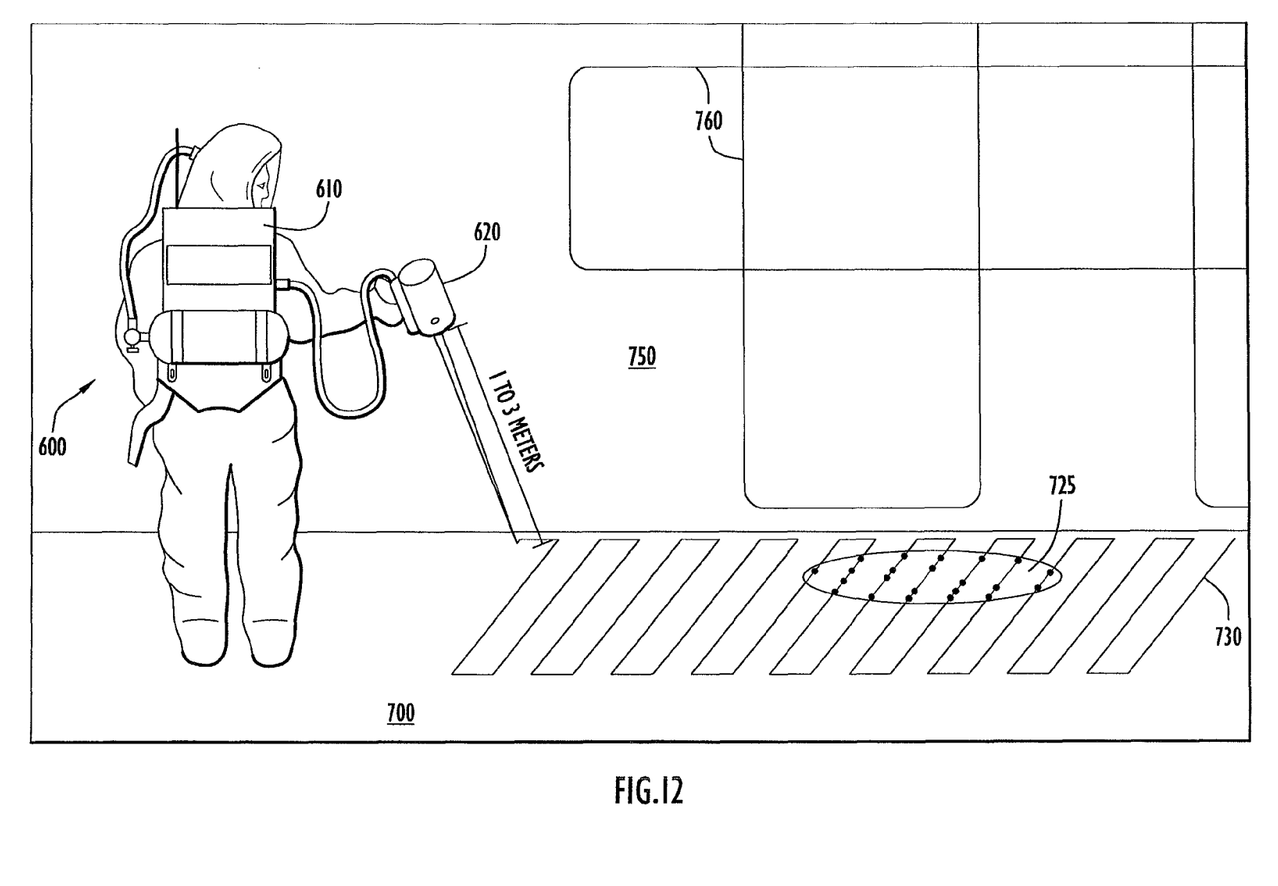
FIG. 12 illustrates an example of a use of the virtual scene generator with a hand-held sensor according to one embodiment.

FIG. 12 illustrates an example of a scene that may be modeled using the techniques described herein. In FIG. 12, a person 600 is shown equipped with a sensor that comprises a body-wearable portion 610 and a hand-held interrogation portion 620. The hand-held interrogation portion 620 is the sensor that is used to simulate actively or passively interrogating a horizontal surface 700 and a vertical surface 750 where substance dispersion is being simulated. On the horizontal surface 700 (e.g., the ground), graphical element lines 730 are drawn to indicate where the detector has already scanned on the surface 700. A substance detection patch is shown at reference numeral 725. The dots in the patch 725 indicate where the interrogation spot overlaps with the substance. Similarly, on a vertical surface 750 (e.g., a wall), graphical element lines 760 are drawn to indicate where on the vertical surface 750 the detector has already scanned.

The system and methods described herein may be embodied in other specific forms without departing from the spirit or essential characteristics thereof. The foregoing embodiments are therefore to be considered in all respects illustrative and not meant to be limiting.

What is claimed is:

1. A method for simulating a scene that has been contaminated with a target substance, comprising:
   receiving from a user information indicative of characteristics of at least one target substance;
   simulating, by a processor, dissemination of the target substance over at least one surface in the scene; and
   simulating, by the processor, detection of the disseminated target substance by a simulated sensor characterized by user-selectable sensor configuration data.

2. The method of claim 1, wherein simulating the dissemination comprises simulating pseudo-random dissemination of the substance in the scene.

3. The method of claim 2, wherein simulating the dissemination comprises:
   selecting a particle size distribution for the target substance; and
   simulating the dissemination in accordance with the particle size distribution.

4. The method of claim 1, wherein receiving the user information comprises receiving from the user information characterizing one or more of: one or more target substances whose dissemination is to be simulated and a quantity of the one or more target substances; one or more interfering substances and quantity of the one or more interfering substances; material of the surface; and size of the scene.

5. The method of claim 4, wherein simulating the dissemination comprises simulating dissemination of the one or more target substances in the presence of the one or more interfering substances on the material of one or more surfaces in the scene.

6. The method of claim 5, wherein simulating the dissemination further comprises simulating physical changes imparted over time to the one or more target substances and the one or more interfering substances due to forces, physical properties, and/or physical phenomena.

7. The method of claim 1, wherein simulating the detection comprises:
   receiving the user-selectable configuration data for the simulated sensor;
   configuring the simulated sensor in accordance with received configuration data;
   simulating interrogation of at least one surface in the scene with the configured sensor; and
   generating data indicative of detection by the configured sensor of the target substance in accordance with the simulated interrogation.

8. The method of claim 7, wherein receiving the configuration data comprises:
   receiving, in the user-selectable configuration data, data that configures the simulated sensor into a passive interrogation mode or an active interrogation mode;
   and simulating the interrogation comprises:
   simulating interrogation of at least one surface in the scene with by the configured sensor to simulate detection of ambient radiation, in the passive interrogation mode, or scattered radiation, in the active interrogation mode, from the surface in the scene.

9. The method of claim 8, wherein receiving the configuration data comprises receiving, in the user-selectable configuration data, data that configures the simulated sensor to sense in an interrogation spot on the surface in the scene of a size established by the configuration of the simulated sensor and simulating the interrogation comprises simulating the interrogation of the surface in accordance with the interrogation spot size.

10. The method of claim 9, wherein for the sensor configured in the active interrogation mode, receiving the user-selectable configuration data further comprises receiving from the user a selection of: size of at least one light beam that is to simulate actively interrogating the surface in the scene; pulse repetition frequency of the light beam; scanning speed of the light beam across the surface and integration time of the sensor.

11. The method of claim 1, wherein simulating the detection comprises generating data indicative of detection of the target substance by a statistical measure dependent on an overlap of an interrogation spot of the simulated sensor having a user-selectable interrogation spot size with the target substance as disseminated in accordance with a user-selectable particle distribution as the sensor is simulated as scanning the surface at a user-selectable scan speed.

12. A method for simulating interrogation of a scene that has been contaminated with at least one target substance, comprising:
simulating, by a processor, dissemination of the at least one target substance in the scene;
simulating, by the processor, interrogation of at least one surface in the scene as contaminated by the simulated dissemination with a simulated sensor in a configuration corresponding to user-selectable configuration data; and
generating, by the processor, data indicative of detection of the at least one target substance by the configured sensor by way of a statistical measure dependent on overlap of an interrogation spot of the configured sensor on the surface with the at least one target substance on the surface in a distribution thereof established by the simulated dissemination, where the interrogation spot is of a size established by the configuration of the simulated sensor.

13. The method of claim 12, further comprising receiving user input data characterizing the at least one target substance, material of the surface, one or more interfering substances and scan speed of the sensor.

14. The method of claim 12, wherein generating the data comprises generating the data where the statistical measure is dependent on a number of overlaps of the interrogation spot with the target substance.

15. The method of claim 12, wherein simulating dissemination further comprises simulating dissemination of at least one interfering substance in the scene.

16. The method of claim 14, and further comprising displaying a map representing the surface, positions of particles of the at least one target substance in the map and positions of the interrogation spot of the sensor in the map.

17. The method of claim 12, wherein simulating the dissemination of the at least one target substance comprises simulating distributing particles of the target substance pseudo-randomly in the scene such that a higher concentration of the particles of the target substance are placed in the scene at regions closer to a dissemination point of the target substance.

18. The method of claim 12, wherein generating the data indicative of the detection comprises generating the data from the statistical measure dependent on the overlap of the interrogation spot with the target substance as a likelihood of detecting the target substance with the simulated sensor simulating a scan of the at least one surface at a user-selectable scan speed.

19. The method of claim 18, wherein generating the data indicative of the detection comprises generating the data from the statistical measure indicative of particle sizes most likely to be interrogated by the simulated sensor.

20. The method of claim 18, wherein generating the data indicative of the detection comprises generating the data from the statistical measure indicative of time needed to scan the scene and record an overlap of the interrogation spot with at least one particle of the target substance with a certain probability of such overlap occurring.

21. A non-transitory computer readable medium storing instructions, that when executed by a computer, cause the computer to simulate a scene that has been contaminated with a target substance, comprising:
receiving from a user information indicative of characteristics of at least one target substance whose dissemination is to be simulated;
simulating dissemination of the target substance over at least one surface in the scene; and
simulating detection of the target substance by a simulated sensor characterized by user-selectable sensor configuration data.

22. The non-transitory computer readable medium of claim 21, wherein the instructions for receiving from a user comprise instructions for receiving user information characterizing one or more of: one or more target substances whose dissemination is to be simulated and a quantity of the one or more target substances; one or more interfering substances and quantity of the one or more interfering substances; material of the surface; and size of the scene.

23. The non-transitory computer readable medium of claim 22, wherein the instructions for simulating the dissemination comprise instructions for simulating dissemination of the one or more target substances in the presence of one or more interfering substances on one or more surfaces of the scene comprising the material.

24. The non-transitory computer readable medium of claim 22, wherein the instructions for simulating the detection comprise:
receiving, in the user-selectable configuration data, data that configures the simulated sensor in a passive interrogation mode or an active interrogation mode; and
simulating interrogation of the at least one surface in the scene by the configured sensor to simulate detection of ambient radiation, in the passive interrogation mode, or scattered radiation, in the active interrogation mode, from the surface in the scene.

25. The non-transitory computer readable medium of claim 21, wherein the instructions for simulating the detection further comprise instructions for generating data indicative of detection of the target substance from a statistical measure dependent on an overlap of an interrogation spot having a user-selectable spot size established by the configuration of the simulated sensor with the target substance as disseminated in accordance with a user-selectable particle distribution as the simulated sensor is simulated as scanning the surface at a user-selectable scan speed.

* * * * *